(12) United States Patent
Colleran et al.

(10) Patent No.: US 7,854,752 B2
(45) Date of Patent: Dec. 21, 2010

(54) SYSTEM AND METHOD FOR DYNAMIC SKELETAL STABILIZATION

(75) Inventors: Dennis Colleran, Frisco, TX (US); Scott Schorer, Plano, TX (US); Paul McAfee, Sparks, MD (US)

(73) Assignee: Theken Spine, LLC, Akron, OH (US)

( * ) Notice: Subject to any disclaimer, the term of this patent is extended or adjusted under 35 U.S.C. 154(b) by 0 days.

(21) Appl. No.: 10/914,751

(22) Filed: Aug. 9, 2004

(65) Prior Publication Data

US 2006/0036240 A1 Feb. 16, 2006

(51) Int. Cl.
*A61B 17/88* (2006.01)
(52) U.S. Cl. ...................................... 606/279
(58) Field of Classification Search ................ 606/61; 623/17.11–17.16
See application file for complete search history.

(56) References Cited

U.S. PATENT DOCUMENTS

| | | | |
|---|---|---|---|
| 1,931,269 A | 10/1933 | Randall | |
| 2,689,756 A | 9/1954 | Carlson | |
| 3,426,364 A | 2/1969 | William | |
| 3,499,222 A | 3/1970 | Limkow et al. | |
| 3,807,394 A | 4/1974 | Attenborough | |
| 3,920,060 A | 11/1975 | Heldmann et al. | |
| 4,157,715 A | 6/1979 | Westerhoff | |
| 4,643,178 A | 2/1987 | Nastari et al. | |
| 4,854,311 A | 8/1989 | Steffee | |
| 5,011,484 A | 4/1991 | Breard | |
| 5,019,080 A | 5/1991 | Hemer | |
| 5,053,036 A | 10/1991 | Perren et al. | |
| 5,092,867 A | 3/1992 | Harms et al. | |
| 5,129,899 A | 7/1992 | Small et al. | |

(Continued)

FOREIGN PATENT DOCUMENTS

EP 0 322 334 6/1989

(Continued)

OTHER PUBLICATIONS

International Search Report & Written Opinion issued for PCT/US2005/027996 dated Mar. 8, 2006.

(Continued)

*Primary Examiner*—Thomas C Barrett
*Assistant Examiner*—Nicholas Woodall
(74) *Attorney, Agent, or Firm*—Middleton Reutlinger; Robert H. Eichenberger; Scott W. Hidgon

(57) ABSTRACT

There is disclosed a system and method for dynamic stabilization which provides for distraction of the inter-vertebral space while still allowing a patient a substantial range of motion. In one embodiment, an inter-vertebral dynamic brace is used to maintain proper distraction. The dynamic brace is designed to allow the vertebrae to which it is attached to move through their natural arc, maintaining the correct instantaneous center of rotation. An adjustable tensioning device is used to maintain the proper distraction and compression forces to restore and maintain proper kinematics, while allowing the dynamic brace to move through an arc centered with respect to the center of rotation of the portion of the spine between the vertebrae. In one embodiment, a method is provided for adjusting the dynamic brace both with respect to the center of rotation of the vertebrae in both the flexion/extension axis and in the superior/inferior axis.

12 Claims, 11 Drawing Sheets

U.S. PATENT DOCUMENTS

| | | |
|---|---|---|
| 5,129,900 A | 7/1992 | Asher et al. |
| 5,151,103 A | 9/1992 | Tepic et al. |
| 5,176,679 A | 1/1993 | Lin |
| 5,196,013 A | 3/1993 | Harms et al. |
| 5,196,014 A | 3/1993 | Lin |
| 5,257,994 A | 11/1993 | Lin |
| 5,261,909 A | 11/1993 | Sutterlin et al. |
| 5,300,073 A | 4/1994 | Ray et al. |
| 5,304,179 A | 4/1994 | Wagner |
| 5,312,404 A | 5/1994 | Asher et al. |
| 5,330,474 A | 7/1994 | Lin |
| 5,375,823 A | 12/1994 | Navas et al. |
| 5,380,324 A | 1/1995 | Muller et al. |
| 5,403,314 A | 4/1995 | Currier |
| 5,413,576 A | 5/1995 | Rivard |
| 5,413,602 A | 5/1995 | Metz-Stavenhagen |
| 5,415,661 A | 5/1995 | Holmes et al. |
| 5,423,816 A | 6/1995 | Lin |
| 5,435,680 A | 7/1995 | Schuster |
| 5,474,551 A | 12/1995 | Finn et al. |
| 5,474,553 A | 12/1995 | Baumgart |
| 5,476,463 A | 12/1995 | Boachie-Adjei et al. |
| 5,480,401 A | 1/1996 | Navas |
| 5,487,744 A | 1/1996 | Howland |
| 5,496,318 A | 3/1996 | Howland et al. |
| 5,498,262 A | 3/1996 | Bryan |
| 5,498,263 A | 3/1996 | DiNelio et al. |
| 5,501,684 A | 3/1996 | Schlapfer |
| 5,520,688 A | 5/1996 | Lin |
| 5,540,687 A | 7/1996 | Fairley et al. |
| 5,540,688 A | 7/1996 | Navas et al. |
| 5,540,690 A | 7/1996 | Miller et al. |
| 5,562,660 A | 10/1996 | Grob |
| 5,562,661 A | 10/1996 | Yoshimi et al. |
| 5,562,662 A | 10/1996 | Brumfield et al. |
| 5,569,248 A | 10/1996 | Mathews |
| 5,575,791 A | 11/1996 | Lin |
| 5,582,612 A | 12/1996 | Lin |
| 5,584,833 A | 12/1996 | Fournet-Fayard et al. |
| 5,584,887 A | 12/1996 | Kambin |
| 5,591,165 A | 1/1997 | Jackson |
| 5,591,166 A | 1/1997 | Bernhardt et al. |
| 5,603,713 A | 2/1997 | Aust et al. |
| 5,609,592 A | 3/1997 | Brumfield |
| 5,609,634 A | 3/1997 | Voydeville |
| 5,611,800 A | 3/1997 | Davis et al. |
| 5,613,968 A | 3/1997 | Lin |
| 5,620,443 A | 4/1997 | Gertzbein et al. |
| 5,628,740 A | 5/1997 | Mullane |
| 5,643,264 A | 7/1997 | Sherman et al. |
| 5,645,599 A * | 7/1997 | Samani .................. 623/17.16 |
| 5,672,175 A | 9/1997 | Martin et al. |
| 5,676,701 A | 10/1997 | Yuan et al. |
| 5,681,313 A | 10/1997 | Diez |
| 5,688,275 A | 11/1997 | Koros et al. |
| 5,704,936 A | 1/1998 | Mazel |
| 5,716,357 A | 2/1998 | Rogozinski |
| 5,725,528 A | 3/1998 | Errico et al. |
| 5,725,582 A | 3/1998 | Bevan et al. |
| 5,733,284 A | 3/1998 | Martin |
| 5,735,851 A | 4/1998 | Errico et al. |
| 5,735,853 A | 4/1998 | Olerud |
| 5,741,255 A | 4/1998 | Kraq et al. |
| 5,800,435 A | 9/1998 | Errico et al. |
| 5,827,286 A | 10/1998 | Incavo et al. |
| 5,836,948 A | 11/1998 | Zucherman et al. |
| 5,846,245 A | 12/1998 | McCarthy et al. |
| 5,855,580 A | 1/1999 | Kreidler et al. |
| 5,860,977 A | 1/1999 | Zucherman et al. |
| 5,876,404 A | 3/1999 | Zucherman et al. |
| 5,879,350 A | 3/1999 | Sherman et al. |
| 5,891,145 A | 4/1999 | Morrison et al. |
| 5,899,902 A | 5/1999 | Brown et al. |
| 5,899,941 A | 5/1999 | Nishijima et al. |
| 5,902,303 A | 5/1999 | Eclipf et al. |
| 5,902,304 A | 5/1999 | Walker et al. |
| 5,944,719 A | 8/1999 | Leban |
| 5,951,553 A | 9/1999 | Betz et al. |
| 5,951,555 A | 9/1999 | Rehak et al. |
| 5,954,722 A | 9/1999 | Bono |
| 5,961,516 A | 10/1999 | Graf |
| 5,964,763 A | 10/1999 | Incavo et al. |
| 5,976,135 A | 11/1999 | Sherman et al. |
| 5,984,924 A | 11/1999 | Asher et al. |
| 5,993,449 A | 11/1999 | Schlapfer et al. |
| 6,017,345 A | 1/2000 | Richelsoph |
| 6,019,769 A | 2/2000 | McCarthy et al. |
| 6,019,792 A | 2/2000 | Cauthen |
| 6,030,388 A | 2/2000 | Yoshimi et al. |
| 6,039,738 A | 3/2000 | Sanders et al. |
| 6,045,552 A | 4/2000 | Zucherman et al. |
| 6,048,342 A | 4/2000 | Zucherman et al. |
| 6,050,997 A | 4/2000 | Mullane |
| 6,063,090 A | 5/2000 | Schlapfer |
| 6,068,630 A | 5/2000 | Zucherman et al. |
| 6,071,519 A | 6/2000 | DeBoer et al. |
| 6,074,390 A | 6/2000 | Zucherman et al. |
| 6,077,262 A | 6/2000 | Schlapfer et al. |
| 6,080,156 A | 6/2000 | Asher et al. |
| 6,083,224 A | 7/2000 | Gertzbein et al. |
| 6,090,112 A | 7/2000 | Zucherman et al. |
| 6,146,383 A | 11/2000 | Studer et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,183,471 B1 | 2/2001 | Zucherman et al. |
| 6,187,005 B1 | 2/2001 | Brace et al. |
| 6,190,387 B1 | 2/2001 | Zucherman et al. |
| 6,228,118 B1 | 5/2001 | Gordon |
| 6,231,575 B1 | 5/2001 | Krag |
| 6,235,030 B1 | 5/2001 | Zucherman et al. |
| 6,235,033 B1 | 5/2001 | Brace et al. |
| 6,235,059 B1 | 5/2001 | Benezech |
| 6,238,397 B1 | 5/2001 | Zucherman et al. |
| 6,241,730 B1 | 6/2001 | Alby |
| 6,241,731 B1 | 6/2001 | Fiz |
| 6,261,288 B1 | 7/2001 | Jackson |
| 6,267,764 B1 | 7/2001 | Elberg et al. |
| 6,267,765 B1 | 7/2001 | Taylor et al. |
| 6,273,889 B1 | 8/2001 | Richelsoph |
| 6,280,444 B1 | 8/2001 | Zucherman et al. |
| 6,280,445 B1 | 8/2001 | Morrison et al. |
| 6,287,308 B1 | 9/2001 | Betz et al. |
| 6,296,644 B1 | 10/2001 | Saurat et al. |
| 6,309,391 B1 | 10/2001 | Crandall et al. |
| 6,315,779 B1 | 11/2001 | Morrison et al. |
| 6,331,179 B1 | 12/2001 | Freid et al. |
| 6,332,882 B1 | 12/2001 | Zucherman et al. |
| 6,332,883 B1 | 12/2001 | Zucherman et al. |
| 6,355,038 B1 | 3/2002 | Pisharodi |
| 6,379,355 B1 | 4/2002 | Zucherman et al. |
| 6,402,750 B1 * | 6/2002 | Atkinson et al. .............. 606/61 |
| 6,413,257 B1 | 7/2002 | Lin et al. |
| 6,416,776 B1 | 7/2002 | Shamie |
| 6,419,676 B1 | 7/2002 | Zucherman et al. |
| 6,419,677 B2 | 7/2002 | Zucherman et al. |
| 6,423,069 B1 | 7/2002 | Sellers |
| 6,440,169 B1 | 8/2002 | Elberg |
| 6,451,019 B1 | 9/2002 | Zucherman et al. |
| 6,451,020 B1 | 9/2002 | Zucherman et al. |
| 6,454,769 B2 | 9/2002 | Wagner et al. |
| 6,471,706 B1 | 10/2002 | Schumacher et al. |
| 6,478,796 B2 | 11/2002 | Zucherman et al. |
| 6,500,178 B2 | 12/2002 | Zucherman et al. |

| Patent | Date | Inventor |
|---|---|---|
| 6,514,256 B2 | 2/2003 | Zucherman et al. |
| 6,520,990 B1 | 2/2003 | Ray |
| 6,529,889 B1 | 3/2003 | Bromberg et al. |
| 6,554,831 B1 | 4/2003 | Rivard et al. |
| 6,575,975 B2 | 6/2003 | Brace et al. |
| 6,582,433 B2 | 6/2003 | Yun |
| 6,585,738 B1 | 7/2003 | Mangione et al. |
| 6,610,062 B2 | 8/2003 | Bailey et al. |
| 6,623,485 B2 | 9/2003 | Doubler et al. |
| 6,626,904 B1 | 9/2003 | Jammet et al. |
| 6,626,909 B2 | 9/2003 | Chin |
| 6,626,944 B1 | 9/2003 | Taylor |
| 6,641,583 B2 | 11/2003 | Shluzas et al. |
| 6,645,207 B2 | 11/2003 | Dixon et al. |
| 6,652,527 B2 | 11/2003 | Zucherman et al. |
| 6,652,534 B2 | 11/2003 | Zucherman et al. |
| 6,663,632 B1 | 12/2003 | Frigg |
| 6,669,697 B1 | 12/2003 | Pisharodi |
| 6,673,074 B2 | 1/2004 | Shluzas |
| 6,679,883 B2 | 1/2004 | Hawkes et al. |
| 6,685,705 B1 | 2/2004 | Taylor |
| 6,689,133 B2 | 2/2004 | Morrison et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,706,068 B2 | 3/2004 | Ferree |
| 6,709,433 B1 | 3/2004 | Schoenefeld |
| 6,712,819 B2 | 3/2004 | Zucherman et al. |
| 6,733,534 B2 | 5/2004 | Sherman |
| 6,740,118 B2 | 5/2004 | Eisermann et al. |
| 6,743,257 B2 | 6/2004 | Castro |
| 6,746,485 B1 | 6/2004 | Zucherman et al. |
| 6,755,830 B2 | 6/2004 | Minfelde |
| 6,761,720 B1 | 7/2004 | Senegas |
| 6,796,983 B1 | 9/2004 | Zucherman et al. |
| 6,802,844 B2 | 10/2004 | Ferree |
| 6,811,567 B2 * | 11/2004 | Reiley .................... 623/17.11 |
| 6,835,205 B2 | 12/2004 | Atkinson et al. |
| 6,852,113 B2 | 2/2005 | Nathanson et al. |
| 6,858,031 B2 | 2/2005 | Morrison et al. |
| 6,884,243 B2 | 4/2005 | Sellers |
| 6,887,242 B2 | 5/2005 | Doubler et al. |
| 6,890,334 B2 | 5/2005 | Brace et al. |
| 6,902,566 B2 | 6/2005 | Zucherman et al. |
| 6,926,728 B2 | 8/2005 | Zucherman et al. |
| 6,936,071 B1 | 8/2005 | Marnay et al. |
| 6,945,972 B2 | 9/2005 | Frigg et al. |
| 6,945,974 B2 | 9/2005 | Dalton |
| 6,945,975 B2 | 9/2005 | Dalton |
| 6,946,000 B2 | 9/2005 | Senegas |
| 6,964,664 B2 | 11/2005 | Freid et al. |
| 6,964,666 B2 | 11/2005 | Jackson |
| 6,966,910 B2 | 11/2005 | Ritland |
| 6,972,020 B1 | 12/2005 | Grayson et al. |
| 6,974,460 B2 | 12/2005 | Carbone et al. |
| 6,979,334 B2 | 12/2005 | Dalton |
| 6,986,771 B2 | 1/2006 | Paul |
| 6,989,011 B2 | 1/2006 | Paul |
| 6,991,632 B2 | 1/2006 | Ritland |
| 7,001,389 B1 | 2/2006 | Navarro et al. |
| RE39,035 E | 3/2006 | Finn et al. |
| 7,011,685 B2 * | 3/2006 | Arnin et al. ............... 623/17.16 |
| 7,029,473 B2 | 4/2006 | Zucherman et al. |
| 7,029,475 B2 | 4/2006 | Panjabi |
| 7,041,136 B2 | 5/2006 | Goble et al. |
| 7,048,736 B2 | 5/2006 | Robinson et al. |
| 7,060,066 B2 | 6/2006 | Zhao et al. |
| 7,074,237 B2 | 7/2006 | Goble et al. |
| 7,083,621 B2 | 8/2006 | Shaolian et al. |
| 7,083,649 B2 | 8/2006 | Zucherman et al. |
| 7,087,083 B2 | 8/2006 | Pasquet et al. |
| 7,101,375 B2 | 9/2006 | Zucherman et al. |
| 7,135,021 B2 | 11/2006 | Lin |
| 7,163,558 B2 | 1/2007 | Senegas et al. |
| 7,182,782 B2 | 2/2007 | Kirschman |
| 7,189,234 B2 | 3/2007 | Zucherman et al. |
| 7,195,632 B2 | 3/2007 | Biedermann et al. |
| 7,195,633 B2 | 3/2007 | Medoff et al. |
| 7,201,751 B2 | 4/2007 | Zucherman et al. |
| 7,204,837 B2 | 4/2007 | Paul |
| 7,207,992 B2 | 4/2007 | Ritland |
| 7,214,227 B2 | 5/2007 | Colleran et al. |
| 7,291,150 B2 | 11/2007 | Graf |
| 2001/0021851 A1 | 9/2001 | Eberlein et al. |
| 2002/0058939 A1 | 5/2002 | Wagner et al. |
| 2002/0095154 A1 | 7/2002 | Atkinson et al. |
| 2002/0133155 A1 | 9/2002 | Ferree |
| 2002/0151978 A1 | 10/2002 | Zacouto et al. |
| 2003/0009226 A1 | 1/2003 | Graf |
| 2003/0028191 A1 | 2/2003 | Shluzas |
| 2003/0055427 A1 | 3/2003 | Graf |
| 2003/0100904 A1 | 5/2003 | Biedermann |
| 2003/0105462 A1 | 6/2003 | Haider |
| 2003/0109880 A1 | 6/2003 | Shirado et al. |
| 2003/0125741 A1 | 7/2003 | Biedermann et al. |
| 2003/0135278 A1 | 7/2003 | Eckman et al. |
| 2003/0153912 A1 | 8/2003 | Graf |
| 2003/0171749 A1 | 9/2003 | Le Couedic et al. |
| 2003/0191470 A1 | 10/2003 | Ritland |
| 2003/0220643 A1 | 11/2003 | Ferree et al. |
| 2004/0002708 A1 | 1/2004 | Ritland |
| 2004/0003039 A1 | 1/2004 | Humphrey et al. |
| 2004/0006342 A1 | 1/2004 | Altarac et al. |
| 2004/0030391 A1 | 2/2004 | Ferree |
| 2004/0049189 A1 | 3/2004 | Le Couedic et al. |
| 2004/0049190 A1 | 3/2004 | Biedermann et al. |
| 2004/0049280 A1 | 3/2004 | Cauthen |
| 2004/0068319 A1 | 4/2004 | Cordaro |
| 2004/0073215 A1 | 4/2004 | Carli |
| 2004/0073307 A1 | 4/2004 | Keller |
| 2004/0078040 A1 | 4/2004 | Feijtel |
| 2004/0092930 A1 | 5/2004 | Petit et al. |
| 2004/0106995 A1 * | 6/2004 | Le Couedic et al. ...... 623/17.11 |
| 2004/0116927 A1 | 6/2004 | Graf |
| 2004/0127897 A1 | 7/2004 | Freid et al. |
| 2004/0143264 A1 | 7/2004 | McAfee |
| 2004/0147928 A1 | 7/2004 | Landry et al. |
| 2004/0153159 A1 | 8/2004 | Cauthen |
| 2004/0181223 A1 | 9/2004 | Ritland |
| 2004/0186577 A1 | 9/2004 | Ferree |
| 2004/0186591 A1 * | 9/2004 | Lang .......................... 623/39 |
| 2004/0193271 A1 | 9/2004 | Fraser et al. |
| 2004/0220570 A1 | 11/2004 | Frigg |
| 2004/0220668 A1 | 11/2004 | Eisermann et al. |
| 2004/0225289 A1 | 11/2004 | Biedermann et al. |
| 2004/0236327 A1 | 11/2004 | Paul et al. |
| 2004/0236329 A1 | 11/2004 | Panjabi |
| 2005/0004573 A1 | 1/2005 | Abdou |
| 2005/0004574 A1 | 1/2005 | Muckter |
| 2005/0010214 A1 | 1/2005 | Tassin |
| 2005/0033432 A1 | 2/2005 | Gordon et al. |
| 2005/0043802 A1 | 2/2005 | Eisermann et al. |
| 2005/0049708 A1 | 3/2005 | Atkinson et al. |
| 2005/0070899 A1 | 3/2005 | Doubler et al. |
| 2005/0070901 A1 | 3/2005 | David |
| 2005/0085813 A1 | 4/2005 | Spitler et al. |
| 2005/0085814 A1 | 4/2005 | Sherman et al. |
| 2005/0090823 A1 | 4/2005 | Bartimus |
| 2005/0102028 A1 | 5/2005 | Arnin et al. |
| 2005/0113927 A1 | 5/2005 | Malek |
| 2005/0125063 A1 | 6/2005 | Matge et al. |
| 2005/0131404 A1 | 6/2005 | Mazda et al. |
| 2005/0131405 A1 | 6/2005 | Molz et al. |
| 2005/0131406 A1 | 6/2005 | Reiley et al. |
| 2005/0131407 A1 | 6/2005 | Sievol et al. |
| 2005/0137594 A1 | 6/2005 | Doubler et al. |

| | | | |
|---|---|---|---|
| 2005/0143737 A1 | 6/2005 | Pafford et al. | |
| 2005/0143823 A1 | 6/2005 | Boyd et al. | |
| 2005/0154392 A1 | 7/2005 | Medoff et al. | |
| 2005/0165398 A1 | 7/2005 | Reiley | |
| 2005/0171540 A1 | 8/2005 | Lim et al. | |
| 2005/0171543 A1 | 8/2005 | Timm et al. | |
| 2005/0177156 A1* | 8/2005 | Timm et al. | 606/61 |
| 2005/0177164 A1 | 8/2005 | Walters et al. | |
| 2005/0177166 A1 | 8/2005 | Timm et al. | |
| 2005/0182400 A1 | 8/2005 | White | |
| 2005/0182409 A1 | 8/2005 | Callahan et al. | |
| 2005/0228386 A1 | 10/2005 | Ziolo et al. | |
| 2005/0245929 A1 | 11/2005 | Winslow | |
| 2005/0256578 A1 | 11/2005 | Blatt et al. | |
| 2005/0261682 A1 | 11/2005 | Ferree | |
| 2005/0261770 A1 | 11/2005 | Kuipe et al. | |
| 2005/0267470 A1 | 12/2005 | McBride | |
| 2005/0288670 A1 | 12/2005 | Panjabi et al. | |
| 2006/0015100 A1 | 1/2006 | Panjabi et al. | |
| 2006/0036240 A1 | 2/2006 | Colleran et al. | |
| 2006/0085076 A1 | 4/2006 | Krishna et al. | |
| 2006/0089717 A1 | 4/2006 | Krishna et al. | |
| 2006/0189983 A1 | 8/2006 | Fallin et al. | |
| 2006/0189984 A1 | 8/2006 | Fallin et al. | |
| 2006/0229613 A1 | 10/2006 | Timm et al. | |
| 2006/0241769 A1 | 10/2006 | Gordon et al. | |
| 2006/0241771 A1 | 10/2006 | Gordon et al. | |
| 2006/0247635 A1 | 11/2006 | Gordon et al. | |
| 2006/0247779 A1 | 11/2006 | Gordon et al. | |
| 2006/0265074 A1 | 11/2006 | Krishna et al. | |
| 2006/0271046 A1 | 11/2006 | Kwak et al. | |
| 2007/0043356 A1 | 2/2007 | Timm et al. | |

FOREIGN PATENT DOCUMENTS

| | | |
|---|---|---|
| EP | 322334 A1 | 6/1989 |
| EP | 0 821 917 | 2/1998 |
| EP | 0669109 A1 | 5/1999 |
| WO | WO-2005087121 | 9/2005 |

OTHER PUBLICATIONS

European Patent Office, International Search Report and Written Opinion, Report, Aug. 22, 2007, pp. 1-14, PCT/US2007/065525, European Patent Office, Rijswijk, the Netherlands.

European Patent Office, International Search Report and Written Opinion, Report, May 10, 2006, pp. 1-18, PCT/US2005/036339, European Patent Office, Rijswijk, the Netherlands.

European Patent Office, International Search Report and Written Opinion, Report, Aug. 22, 2007, pp. 1-15, PCT/US2004/035000, European Patent Office, Rijswijk, the Netherlands.

* cited by examiner

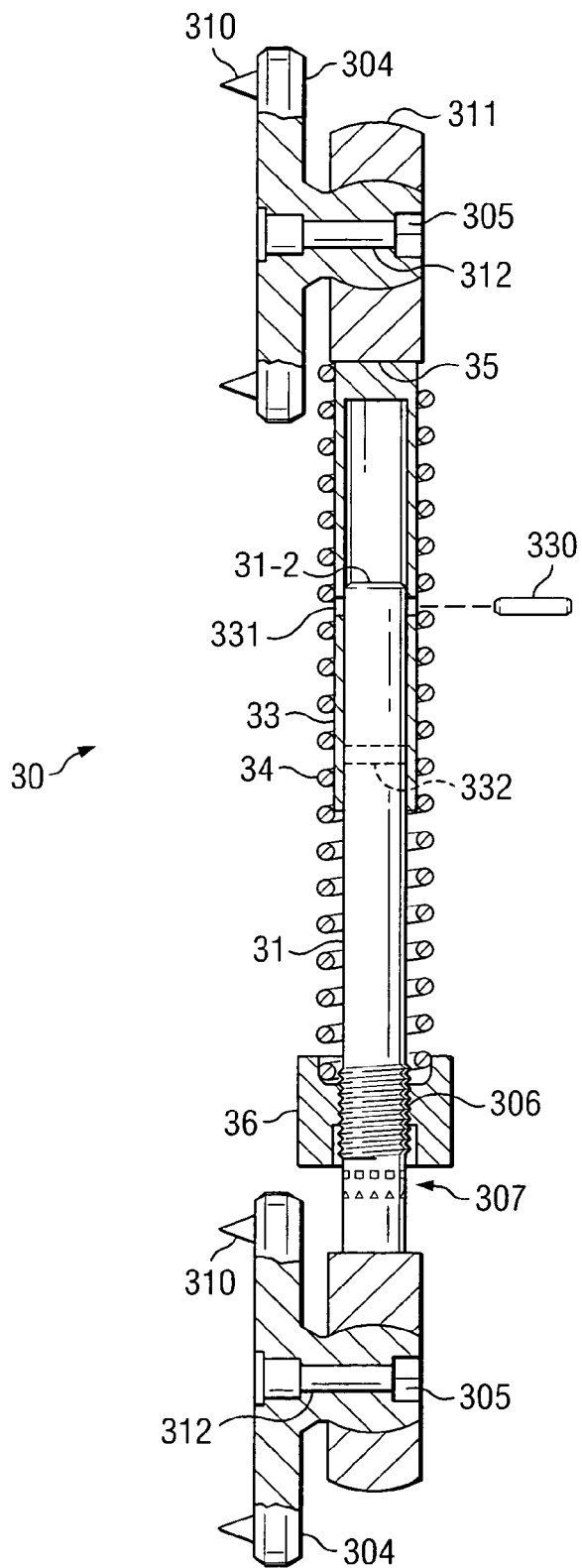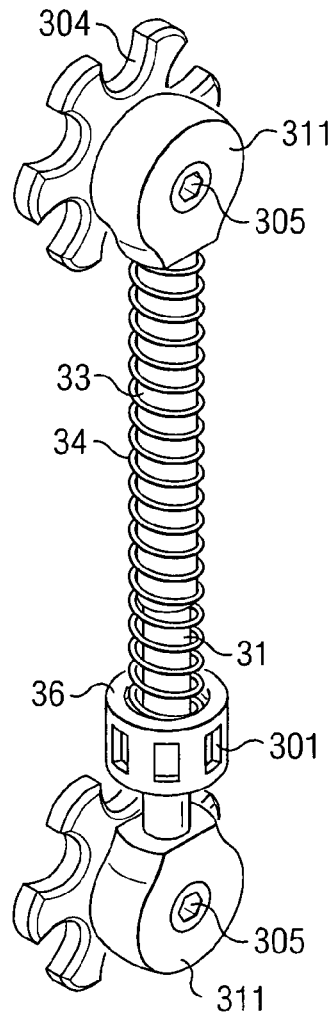

SYSTEM AND METHOD FOR DYNAMIC SKELETAL STABILIZATION

CROSS-REFERENCE TO RELATED APPLICATIONS

The present application is related to co-pending, and commonly assigned U.S. patent application Ser. No. 10/690,211, entitled "SYSTEM AND METHOD FOR STABILIZING INTERNAL STRUCTURES," filed Oct. 21, 2003, the disclosure of which is hereby incorporated herein by reference.

TECHNICAL FIELD

This disclosure relates to skeletal stabilization and more particularly to systems and methods for stabilization of human spines and even more particularly to dynamic stabilization techniques.

BACKGROUND OF THE INVENTION

The skeletal system, particularly the human spine, is a complex structure designed to achieve a myriad of tasks, many of them of a complex kinematic nature. While performing its function, the spine must move into flexion (bending forward) and extension (bending backward). For example, the vertebrae that make up the lumbar region of the human spine move through roughly an arc of 15° relative to its neighbor vertebrae. Vertebrae of other regions of the human spine (e.g., the thoracic and cervical regions) have different ranges of movement. Thus, if one were to view the posterior edge of a healthy vertebrae one would observe that the edge moves through an arc of some degree (e.g., of about 15° if in the lumbar region) centered around an elliptical center of rotation. The inter-vertebral spacing in a healthy spine is maintained by a compressible disc which serves to allow the spine to move through this arc.

In situations (based upon injury or otherwise) where a disc is not functioning properly, the inter-vertebral disc tends to compress, and in doing so pressure is exerted on nerves extending from the spinal cord by this reduced inter-vertebral spacing. Various other types of nerve problems may be experienced in the spine, such as exiting nerve root compression in neural foramen, passing nerve root compression, and ennervated annulus (where nerves grow into a cracked/compromised annulus, causing pain every time the disc/annulus is compressed), as examples. Many medical procedures have been devised to alleviate such nerve compression and the pain that results from nerve pressure. Many of these procedures revolve around attempts to prevent the vertebrae from moving too close to each other thereby maintaining space for the nerves to exit without being impinged upon by movements of the spine.

One such attempt is shown in U.S. Pat. No. 6,048,342 (hereinafter "the '342 patent") in which screws are embedded in adjacent vertebrae pedicles and rigid spacers are then sewed between the screws. In such a situation, the pedicle screws (which are in effect extensions of the vertebrae) then press against the rigid spacer which serves to distract the degenerated disc space so as to prevent the vertebrae from compressing the nerves. This works for preventing nerve pressure due to extension of the spine, however when the patient then tries to bend forward (putting the spine in flexion) the posterior portions of at least two vertebrae are effectively tied together and thus can not move through any arc, let alone through 15° of motion desired for some regions of the spine. This not only limits the patient's movements but also places additional stress on other portions of the spine (typically, the stress placed on adjacent vertebrae being the worse), often leading to further complications at a later date.

In some approaches, such as shown in European Patent Publication 01/45,576 A1, a "stop" is placed between spinous processes and the spinous processes are then banded together. This procedure has the same limitations and drawbacks as discussed above for the '342 patent.

In still another attempt to solve the compression problem, a lever arm approach has been attempted, as shown in U.S. Pat. No. 6,290,700, again resulting in the same problems, namely, an effective "welding" of two vertebrae together.

U.S. Patent Application Publication No. US/2004/002708A1 (hereafter "the '708 publication") with a Publication Date of Jan. 1, 2004 is entitled, "DYNAMIC FIXATION DEVICE AND METHOD OF USE" shows a dynamic fixation device that allows flexion. The device and method of the '708 publication uses a geometric shape to allow flexion but makes no provision for preventing or reducing disc compression during such flexion.

BRIEF SUMMARY OF THE INVENTION

There is disclosed a system and method for dynamic stabilization which provides for distraction of the inter-vertebral space while still allowing a patient a substantial range of motion. In one embodiment, an inter-vertebral dynamic brace is used to maintain proper distraction. The dynamic brace is designed to allow the vertebrae to which it is attached to move through its natural arc. An adjustable compression device is used to maintain the proper distraction force while allowing the dynamic brace to move through an arc centered with respect to the center of rotation of the portion of the spine between the distracted vertebrae. Accordingly, such dynamic brace aids in permitting a substantial range of motion in flexion, extension, and/or other desired types of spinal motion.

In one embodiment, a method is provided for adjusting the dynamic brace, both with respect to the center of rotation of the distracted vertebrae in both the flexion/extension axis and in the superior/inferior axis.

In a still further embodiment, the spring tension is adjustable on a patient by patient basis to take into account body weight and strength as well as physical characteristics of the patient's skeletal system. Also, provisions may be made to convert the dynamic brace to a static brace while the device remains in situ.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which:

FIGS. 3A, 3B and 3C show one embodiment of a dynamic brace used for spinous process stabilization;

DETAILED DESCRIPTION OF THE INVENTION

Figure 1:
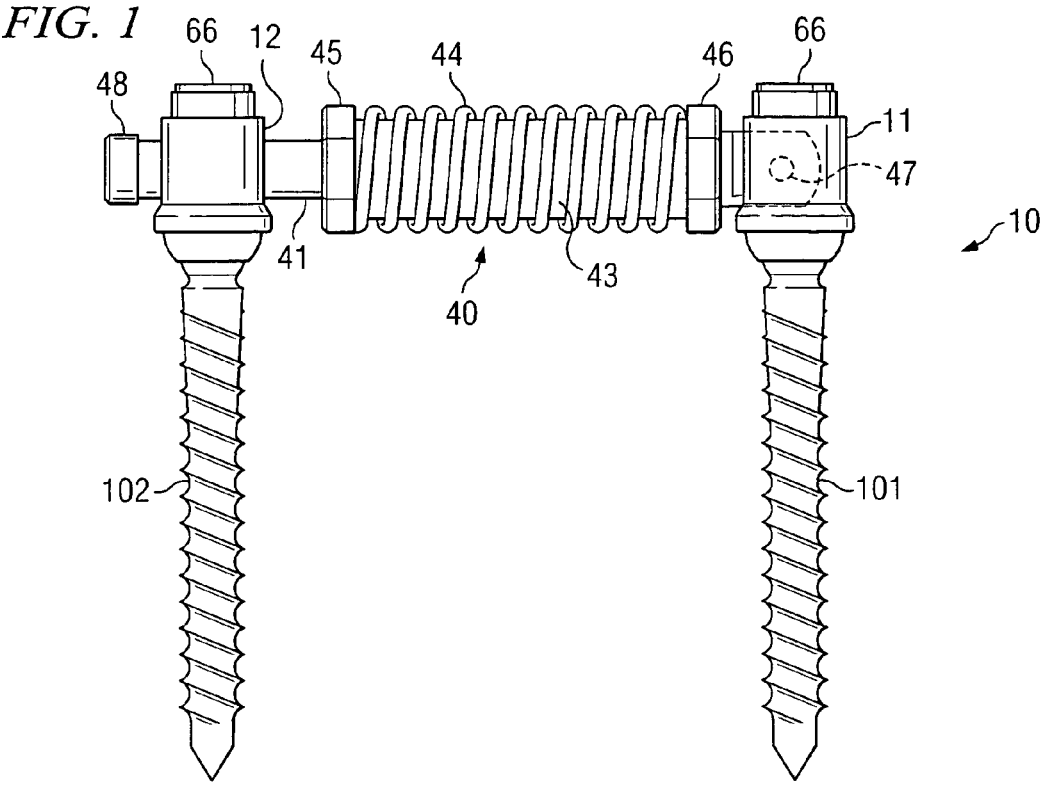
FIG. 1 shows one embodiment of a dynamic brace fitted between a pair of bone anchors.

FIG. 1 shows dynamic brace (or "rod") 40 positioned with respect to pedicle screws 101 and 102 in system 10. This is but one embodiment of the manner in which a dynamic stabilization device can be employed to partially off-load (or un-weight) the disc between vertebrae (to reduce compression forces) so that as the spine moves through its normal range of motion pressure on the disc is reduced throughout the entire range of motion. In this embodiment, the pedicle screws are positioned in the pedicles of the spine as discussed and shown in the above-identified co-pending U.S. Patent Application entitled "SYSTEM AND METHOD FOR STABILIZING INTERNAL STRUCTURES." FIGS. 6A through 6F discussed below show in more detail how and where the pedicle screws are implanted for a dynamic brace in accordance with one procedure.

As will be discussed, one of the purposes of the dynamic brace is so that as adjacent pedicles move with respect to each other they are free to follow their natural motion around a center of rotation. In certain embodiments, some amount of translation is permitted such that the center of rotation need not be a fixed point. As shown in FIG. 1, brace portions 41 and 43 of dynamic brace 40 are free to move with respect to each other along their longitude axis in a telescoping manner. This motion is controlled, in part, by spring 44. Stop 46, working in conjunction with stop 45, serves to allow spring 44 (or springs) to be effectively lengthened or shortened thereby changing the force the spring exerts which, in turn, changes the force between brace portions 41 and 43. The relative movement between brace portions 41 and 43, which could be a tube within a tube, allows for 5° to 20° flexion of the vertebrae to which it is attached in certain embodiments. Of course, the implementation of brace 40 may be adapted to allow for any desired range of flexion in alternative embodiments. In addition, as will be detailed, dynamic brace 40, as it bends, will maintain a correct biomechanical center of rotation, which is not necessarily limited to a fixed center of rotation, with respect to the vertebrae while also reducing or eliminating pressure on the disc between the vertebrae. This partial off-loading of the disc is accomplished by the rigid nature of the rod and spring assembly. While various embodiments are described herein as employing a spring for achieving the permissible degree of movement in the brace, other devices will be readily recognized for substituting for this function, such as employing a hydraulic, pneumatic or other distracting system. If rotation of the device becomes an issue, the telescoping portions can be designed, for example, using an interlocking groove or using matched longitudinal channels, one in each tube, to prevent relative rotation.

Also, as will be seen, by changing the position where head 12 grips portion 41, the center of rotation in a superior/inferior axis of rotation along the patient's skeletal anatomy can be adjusted. Dynamic brace 40 can be adjusted to create a proper distraction height prior to being implanted and thereafter can be adjusted to the desired distraction force in situ. Because the spine is free (subject to constrained motion) to bend, multiple dynamic braces can be used along the spine while still allowing the spine to move into flexion and, if desired, extension. In certain procedures, the dynamic brace 40 may be, for example, be positioned and correctly tensioned/adjusted in communication with a device that determines a patient's spinal neutral zone.

Figure 2A:
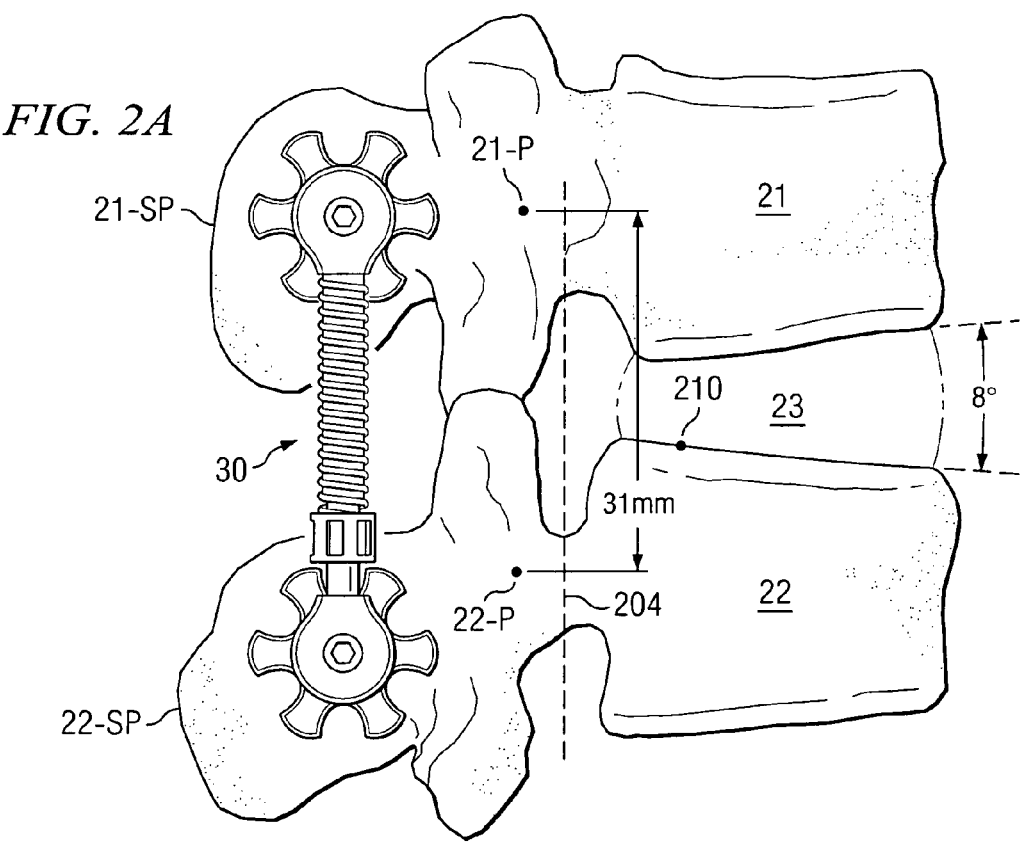
FIGS. 2A, 2B and 2C show one embodiment of a dynamic brace fitted between adjacent spinous processes.
Figure 2B:
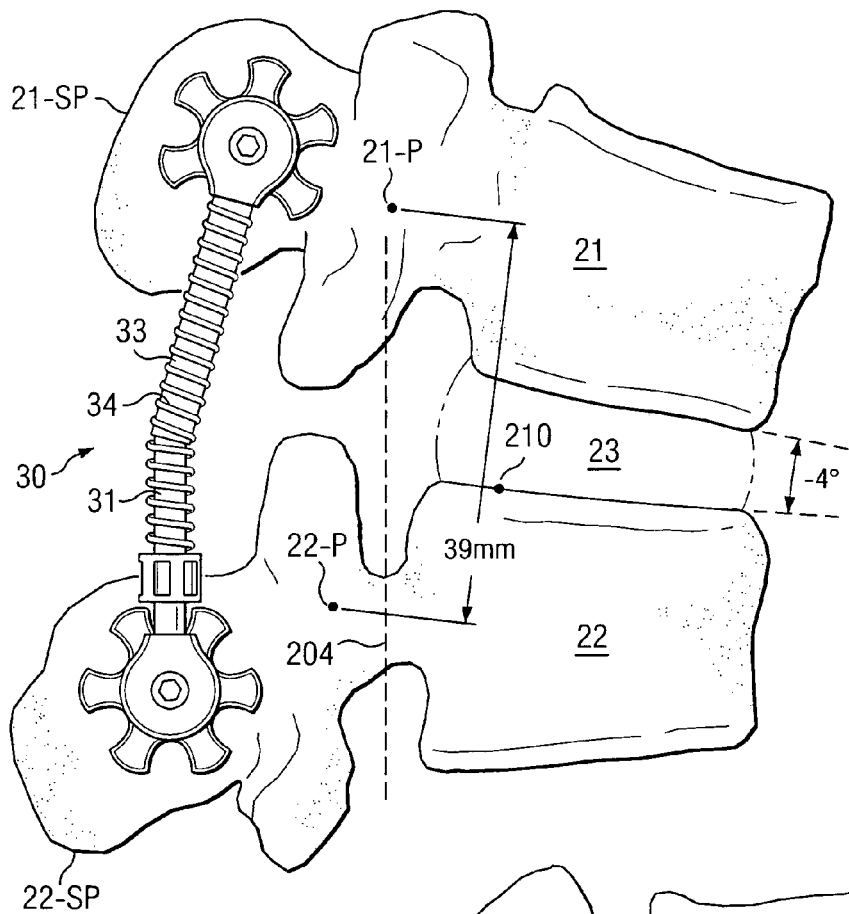
Figure 2C:
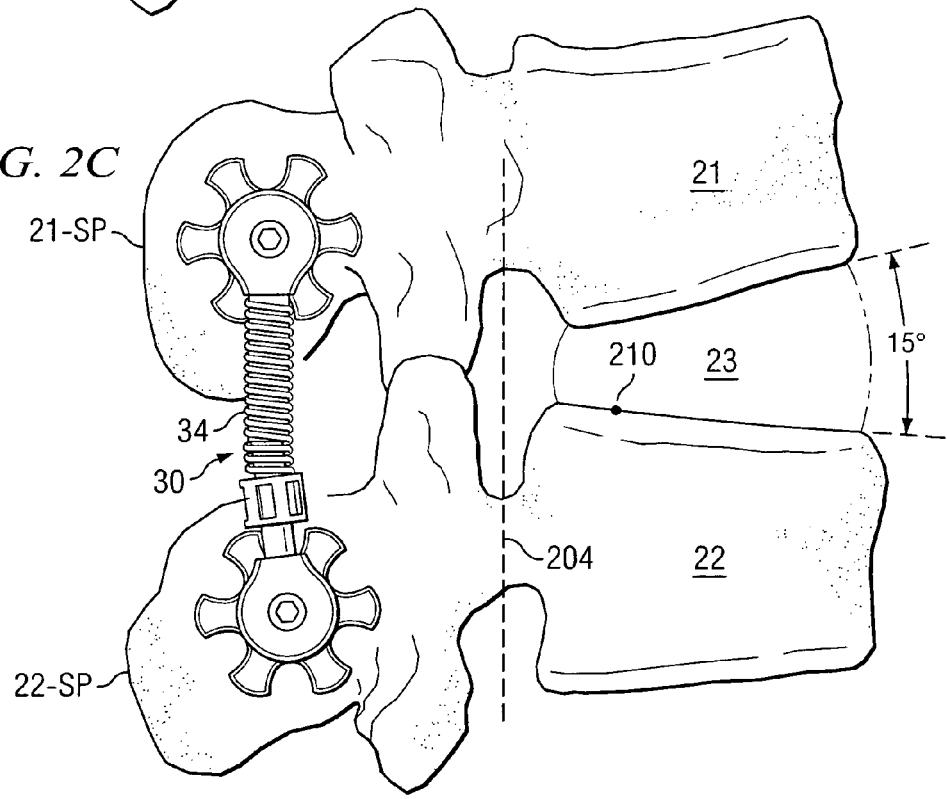

FIGS. 2A to 2C show a dynamic stabilization device being used across adjacent spinous processes 21-SP-22-SP as opposed to being in the pedicles, such as in pedicle 22-P and pedicle 21-P. FIG. 2A shows two vertebrae 21 and 22 (which could, for example, be L4, L5 or any other vertebrae) separated by disc 23. Space 204 between vertebrae 21 and 22 is where nerves would typically emerge from the spinal column. FIG. 2A shows the skeletal system in the neutral position. In this position, the angle between the generally horizontal planes defined by end-plates of the adjacent vertebrae could be, for example, 8°. Note that, while not shown, an extension (or a stabilization device 30) could extend to a next adjacent spinous process if multiple vertebrae are to be stabilized. The center of rotation for this vertebral pair is 210. Note that while this embodiment is shown as a mated pair, it can be used unilaterally. Also note that the attachment to the spinous process should be as anterior on the spinous process as practical. The junction of the lamina and the spinous process would be a strong fixation point.

FIG. 2B shows the dynamic stabilization device 30 with vertebrae 21 and 22 in the flexed position. Note that in the illustration spinous process 21-SP has moved up and into the right (anterior) as the spine is bent forward (flexion). A typical movement distance for the posterior of the spinous process is patient specific and would be approximately 4-16 mm. Spring 34 has expanded along with the dynamic brace to allow spinous process 21-SP to move upward and forward rotating about center of rotation 210. As will be discussed hereinafter, the center of rotation is not a constant point but will move in an ellipse or centroid as the vertebrae move from extension to flexion.

When fully in flexion, the front surfaces of vertebrae 21 and 22 form an angle of, for example, −4°, which is a change of 12° from the neutral position. Assuming the vertebrae goes into extension by, for example, 3°, the total range of motion is about 15° as shown in FIG. 2C. Ideally, the center of rotation would be around the location shown as 210. The center of rotation of the spine does not change from flexion to extension or with side bending. However, the "Instantaneous Axis of Rotation" (IAR) changes throughout the rotation arc. The sum of all of the IARs is therefore one point which is called the Center of Rotation "COR). When the spine moves through flexion and extension the motion of the adjacent vertebrae can be an arc defined by 5 points as shown. The dynamic brace can be adjusted to move the center of rotation 210 forward-backward (X axis) and upward-downward (Y axis), as will be discussed.

In FIG. 2B, spring 34 serves to pull the spinous process back together thereby limiting the compression applied to nerves extending from 204. Note that as between FIGS. 2A and 2B the respective pedicles have separated by approximately 8 mm. The range shown (31 mm to 39 mm) is but one example. Other patients would have other starting and ending points depending upon their particular physical structure and medical condition. The important point being that the pedicles (vertebrae) and facets can move through their natural range of motion and thus separate during flexion.

In FIG. 2C, spring 34 serves to stabilize the spine when in extension. In both cases, the limit of movement is controlled by the limits of brace portions 31 and 33 along their longitudinal length.

Figure 3C:
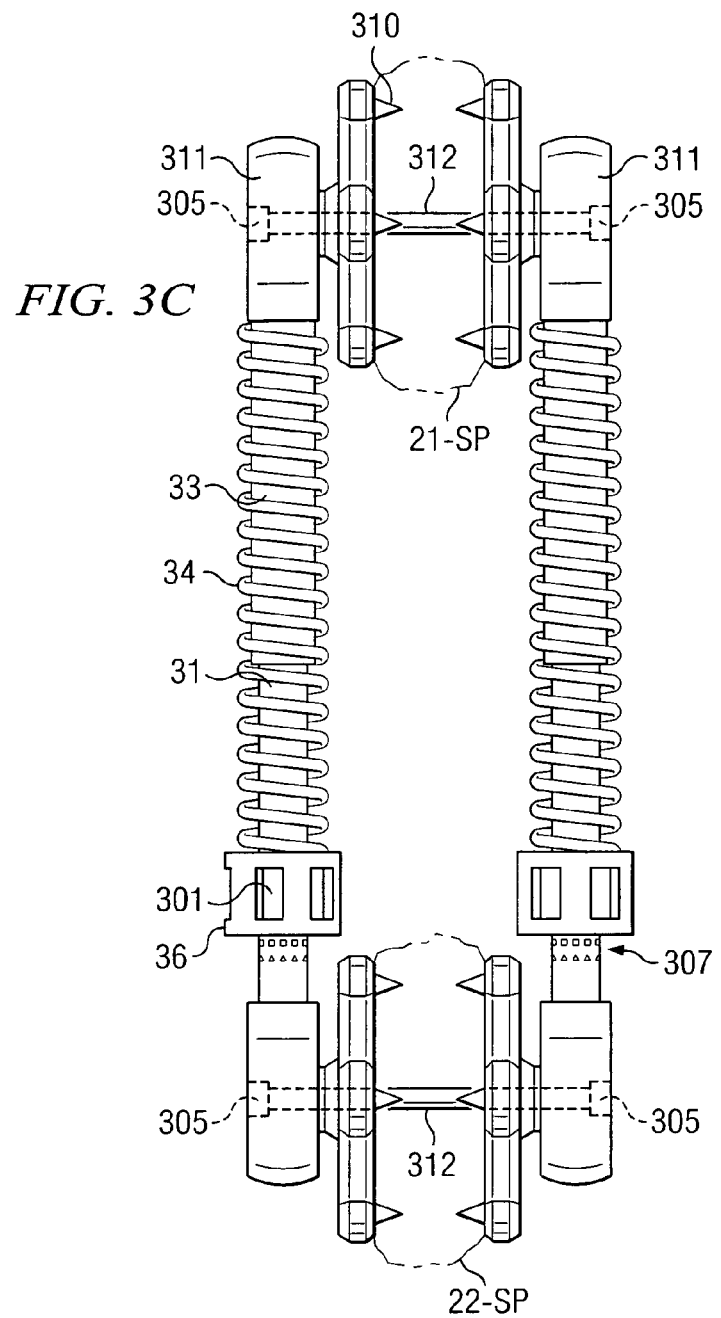

FIG. 3A shows a cross-section of the one embodiment of spinous process dynamic device 30 having an external spring and a pair of expandable brace portions 31 and 33. Portion 31, which can be a solid rod, if desired, (or any other suitable structure, such as a tube, a plurality of parallel-arranged rods or tubes, etc.) moves inside portion 33 which can be a hollow tube. External of both of these portions is spring 34, the tension of which is controlled by stop 36 tightening (or loosening) under control of openings 301 (FIG. 3B). Stop 36 in this embodiment works in cooperation with threads 306. Note that any type of stop can be used, thread or threadless and the stop(s) can be inside the rod or outside. Dynamic stabilization device (or "brace" or "rod") 30 can be attached to either side of the spinous process or could be used in pairs interconnected by rod 312 (FIG. 3C).

As shown in FIG. 3A, as the spinous process moves into flexion, brace portion 33 moves upward. Brace portion 31 remain relatively stationary and thus rod end 31-2 moves down (relatively) inside portion 33. This expansion and contraction along the lateral length of device 30 allows the spine to follow a normal physiologic motion during bending of the spine.

Forward, lateral and twisting motion of device 30 are accomplished by spherical bearing 311 which is free to move in three planes or axis around spherical end support 312.

Stop 36 is moved to adjust tension or spring 34—as it is moved upward (toward stop 35) force increases and as it moves downward force decreases. Force marks (e.g., triangles and squares 307 shown in this example) embossed (or otherwise marked) on shaft 31 aid the surgeon in adjustment of the spring force. Thus, for instance, if the triangles are showing the spring force could be, for example, 30 pounds and if the squares are showing the spring force is known to be, for example, 60 pounds. This pre-calibration helps the installation process. Note that the spacing between these force marks in the drawing are arbitrarily drawn in this example, but may be implemented so as to represent the difference between forces.

Load transfer plates 304 help distribute the forces between the respective vertebrae. Spikes 310 can be used for better load distribution to the spinous process.

FIG. 3B shows device 30 from a perspective view. Bearings 311, of dynamic stabilization device 30, revolve around rod end bearings 312 and allow rotation of the brace for flexion/extension; lateral bending and trunk rotation. Fastener 305 serves to hold the brace to the end support.

FIG. 3C shows one embodiment of a pair of dynamic stabilization devices connected on either side of spinous process 21-SP (22-SP). Device 30 is installed by creating a hole (by drilling or other means) in each spinous process and screwing (or otherwise connecting) rod 312 through the created hole to interconnect the two internally separated devices, as shown.

Figure 4A:
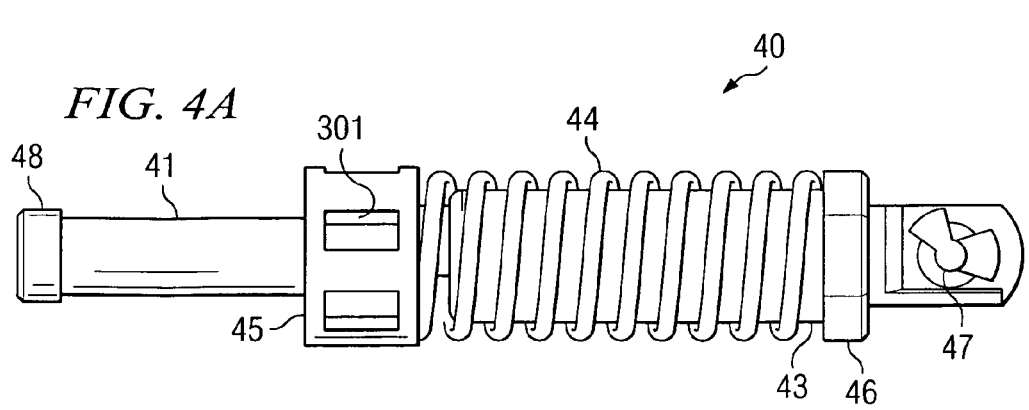
FIGS. 4A, 4B and 4C show one embodiment of a dynamic brace used for pedicle screw stabilization.

FIG. 4A shows another example embodiment of a dynamic stabilization device 40 for use between bone anchors, such as, for example, pedicle screws. Device 40 is constructed similar to device 30 except that the ends are held in position by pedicle screws. Portion 47 is attached to one pedicle screw while portion 41 is held by a second pedicle screw. Adjustment along the Y-axis is achieved by moving the position along portion 41 where the pedicle anchor is clamped to device 40. This effectively changes the neutral length of device 40.

Figure 4B:
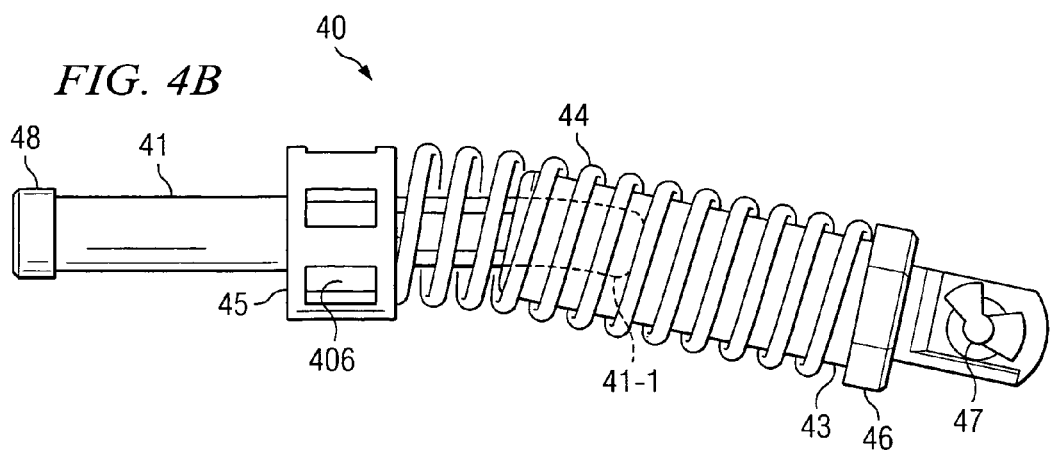

FIG. 4B shows device 40 extended when the spine is in flexion. Device 40 extends around a curvilinear path (as will be detailed with respect to FIG. 4C) and the spring length increases, in this example, from approximately 0.745 to 0.900 inches. Spring deflection is 0.155 inches. End 48 of device 41 is assumed in a fixed position while end 47 moves superior (right) and exterior (down) with respect to end 48. Of course, other dimensions of increase in length and deflection may be achieved in other uses. That is, different amounts of flexion and extension may be permitted in certain patients.

Figure 4C:
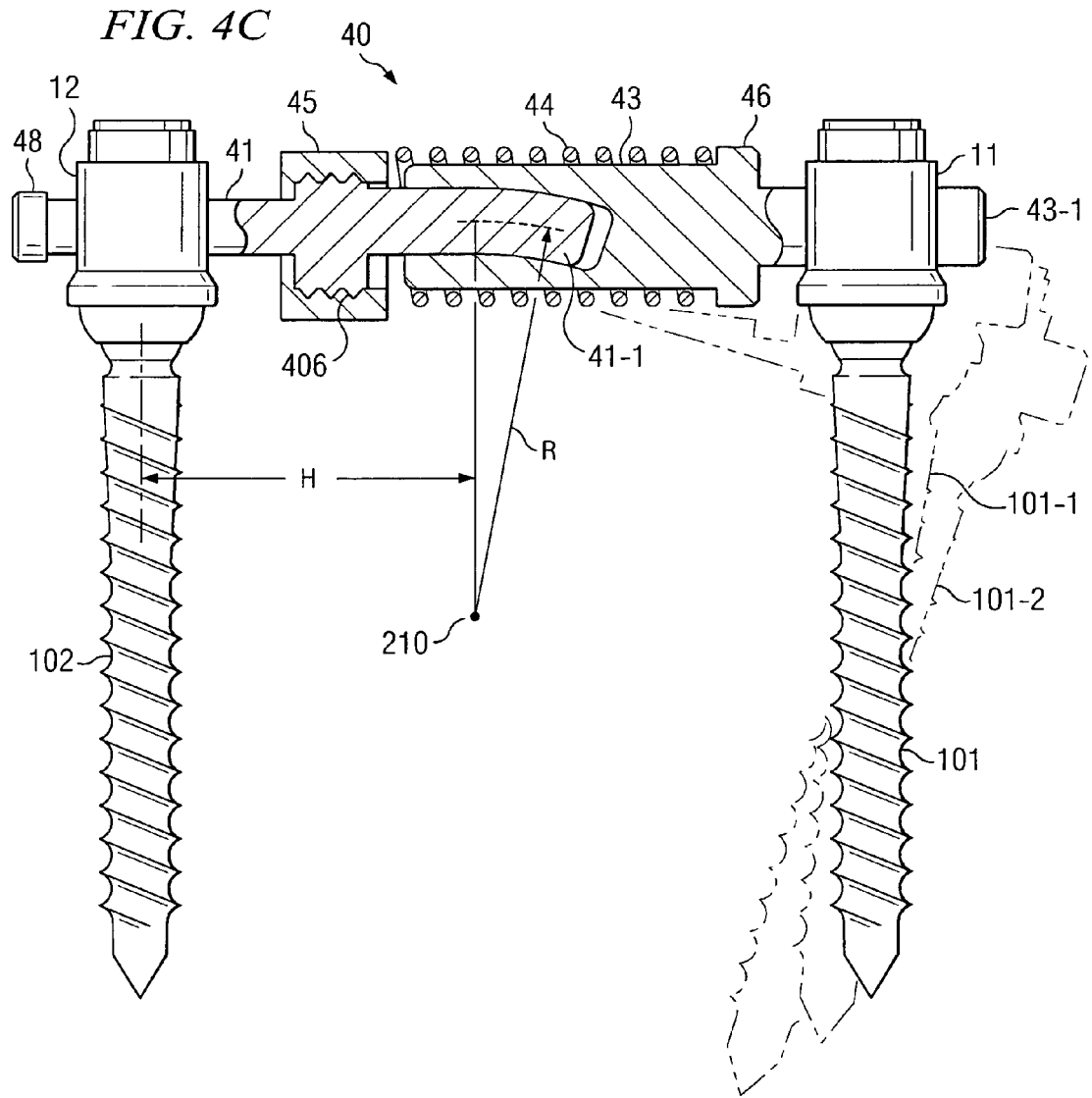

FIG. 4C shows device 40 attached to pedicle screws 101 and 102. One end of portion 41 is held captive by head 12 positioned at the top of pedicle screw 102 by a polyaxial connection. Portion 43 of dynamic stabilization device 40 slides over curved guide portion 41-1 of portion 41. In this embodiment, portion 41 (and 41-1) can be hollow or solid and portion 43 will be hollow. End 43-1 of portion 43 is held captive by head 11 polyaxially mounted to pedicle screw (or other type of bone anchor) 101. Note that end 43-1 may be adjusted to extend beyond head 11 prior to being clamped into head 11 if it is necessary to allow for a greater range of travel of end 41-1 within tube 43. For example, this may be necessary for closely placed bone anchors. As discussed, spring 44 is positioned around the outside of portion 43 between stops 45 and 46. Spring 44 is held in compression and adjusted by rotatable stop 45 moving under control of threads 406.

As discussed, guide 41-1 fits inside of portion 43 and is curved. It is this curve that allows pedicle screw 101 to move in an arc (as shown) when the pedicle to which screw 101 is attached rotates in flexion. This allows dynamic stabilization device 40 to rotate about center of rotation 210 with a natural motion. Natural meaning how the spine would have moved had it been working properly. Note that the X-axis center of rotation of device 40 is controlled by the bend of guide 41-1 relative to portion 43. As discussed above, the center of rotation in the superior/inferior axis (Y-axis) is controlled by the position of end 48 with respect to the pedicle screw 102.

Positions 101-1 and 101-2 of pedicel screw 101 shows pedicle screw kinematic analysis as the spine moves into flexion. As shown, pedicle screw 101 goes through a range of arc motion around center of rotation 210. It is this range of arc motion that the stabilization device tries to maintain.

Figure 5A:
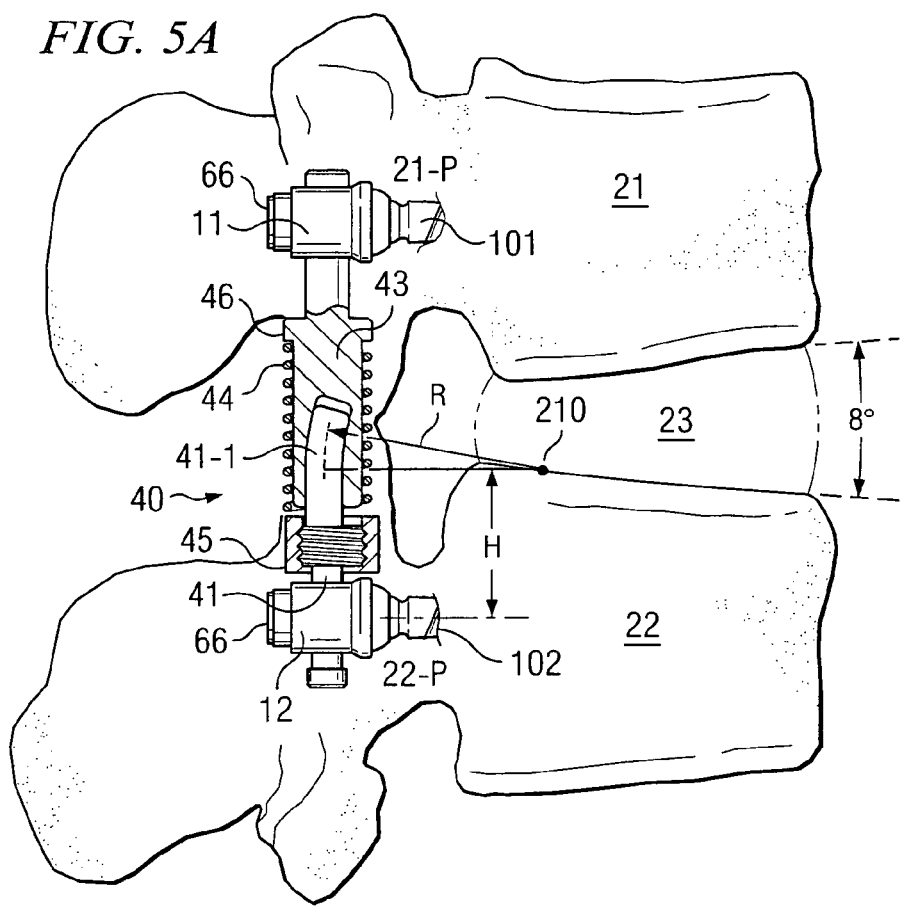
FIGS. 5A and 5B illustrate the movement of the center of rotation between a pair of adjacent vertebrae.
Figure 6A:
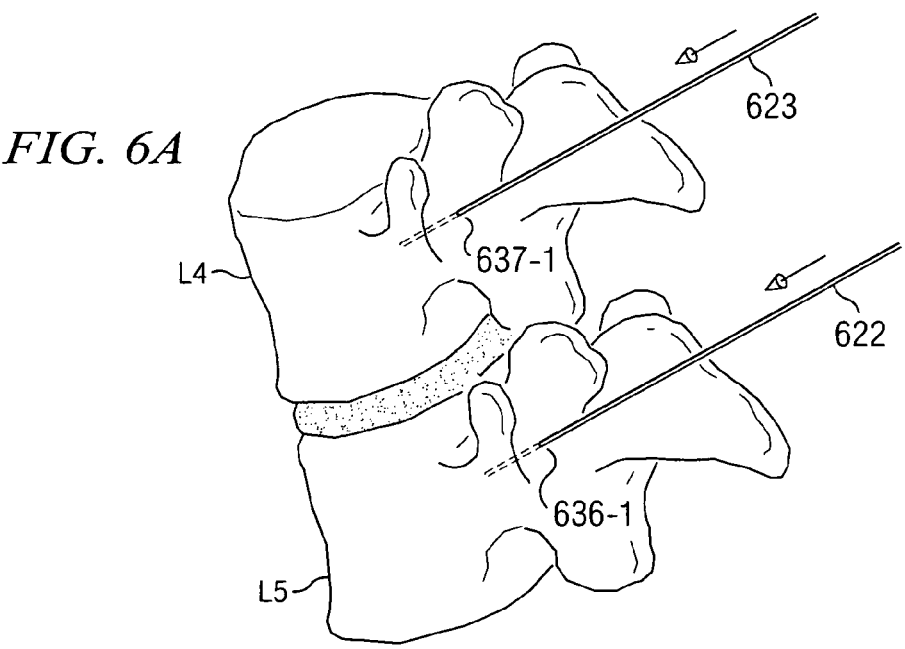
FIGS. 6A, 6B, 6C, 6D, 6E and 6F show one embodiment of a procedure for implanting a dynamic brace to implanted pedicle screws.

FIG. 5A shows dynamic stabilization device 40 positioned in pedicles 21-P, 22-P of vertebrae 21, 22, respectively. The length of the device between heads 11 and 12 is adjusted during implantation such that dimension H positions the length by tightening locks 66 when the H dimension is as desired. This, as discussed, is the (Y) axis (or superior/inferior) of adjustment. The curvilinear motion is set with respect to the R dimension and this is the (X) axis (or flexion/extension) of adjustment. The (X) and (Y) dimensions are set with reference to the desired center of rotation 210. The force provided by spring 44 in combination with portions 41 and 43 keep vertebrae 21 from pressing too heavily on disc 23 thereby partially off-loading the intervertebral disc.

Figure 5B:
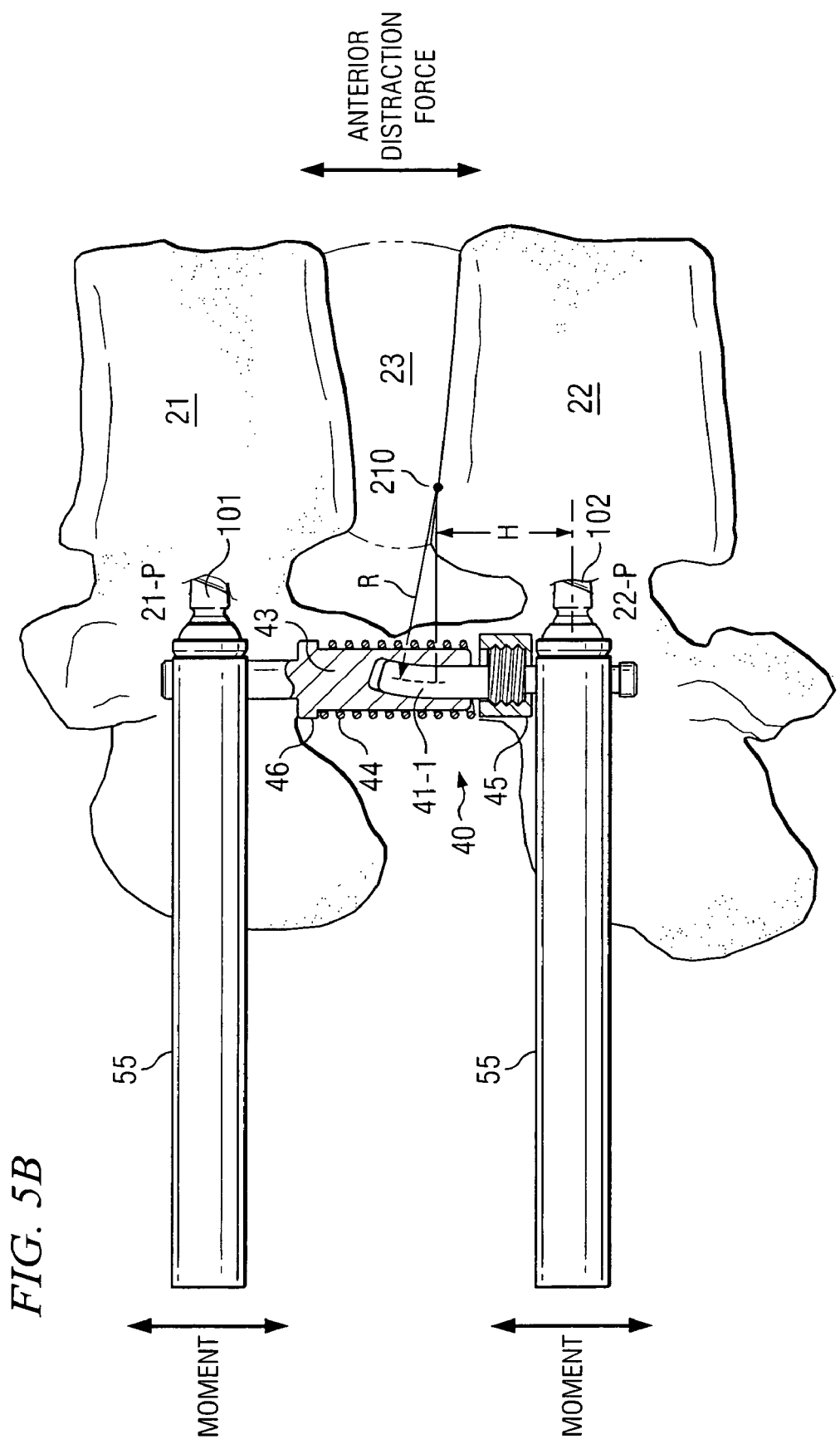

FIG. 5B shows that by applying a moment about extensions 55 and then locking down the length of device 40 there can be created an anterior distraction force on vertebral bodies 21, 22. This will more evenly distribute the loading on disc 23 thereby creating a more optimal environment for the disc when compared to only a posterior distracting implant system. Extensions 55 are removed after the proper length of device 40 is achieved.

FIGS. 6A-6F show one procedure to insert the dynamic brace between vertebrae, such as vertebrae L5 (21) and L4 (22). This procedure is detailed in the above-identified patent application and is repeated herein for convenience. The surgeon identifies the desired vertebral levels and pedicle positions via standard techniques. Once the target vertebrae are identified, a small incision is made through the skin and a tracking needle (or other device) is inserted to pinpoint exactly where each anchor is to be placed. A fluoroscope, or other x-ray technique, is used to properly position the tracking needle. Once the proper position is located, guide wire (K wire) 622 (FIG. 6A) is positioned with its distal end against the pedicle, in this case pedicle 636-1 of vertebrae L5. A guide wire 623 may be similarly positioned with its distal end against/within pedicle 637-1 of vertebrae L4.

Figure 6B:
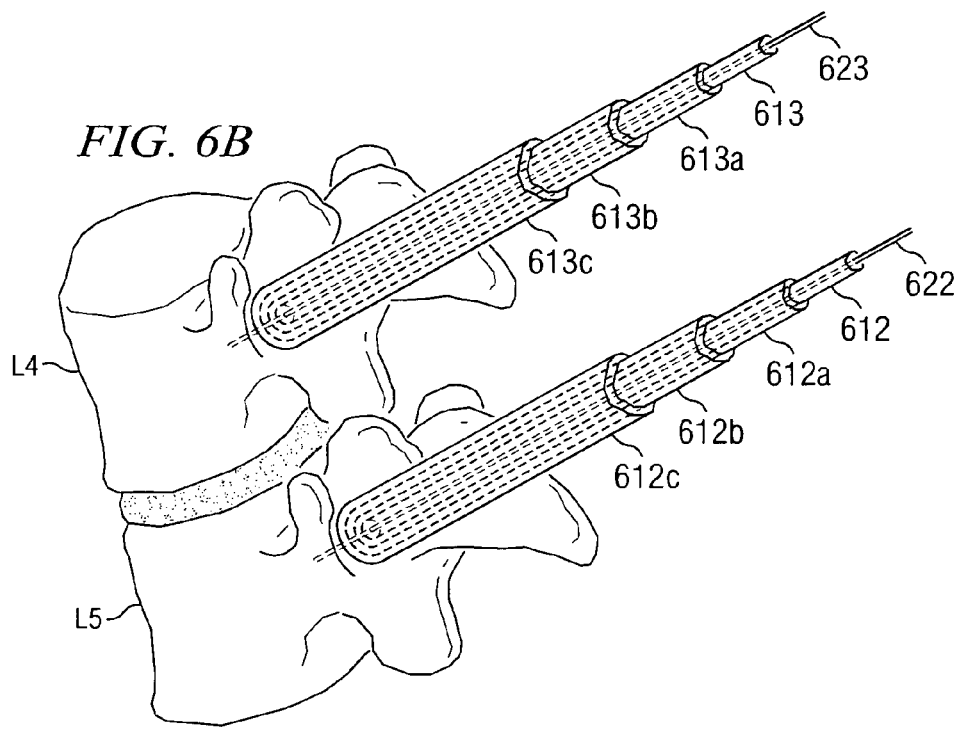

As shown in FIG. 6B the surgeon then slides a series of continuing larger sized dilators 612, 612a, 612b, 612c down guide wire 622, and slides a series of continuing larger sized dilators 613, 613a, 613b, 613c down wire 623.

Approximately four or five dilators are used until a diameter suitable for passing the anchor and its extensions is achieved. A tap is inserted over the K wire to tap a hole into the pedicle in preparation for receiving the anchor, which in this case is a pedicle screw. This tap will usually be a size slightly smaller than the pedicle screw thread size selected for that patient and that level.

Figure 6C:
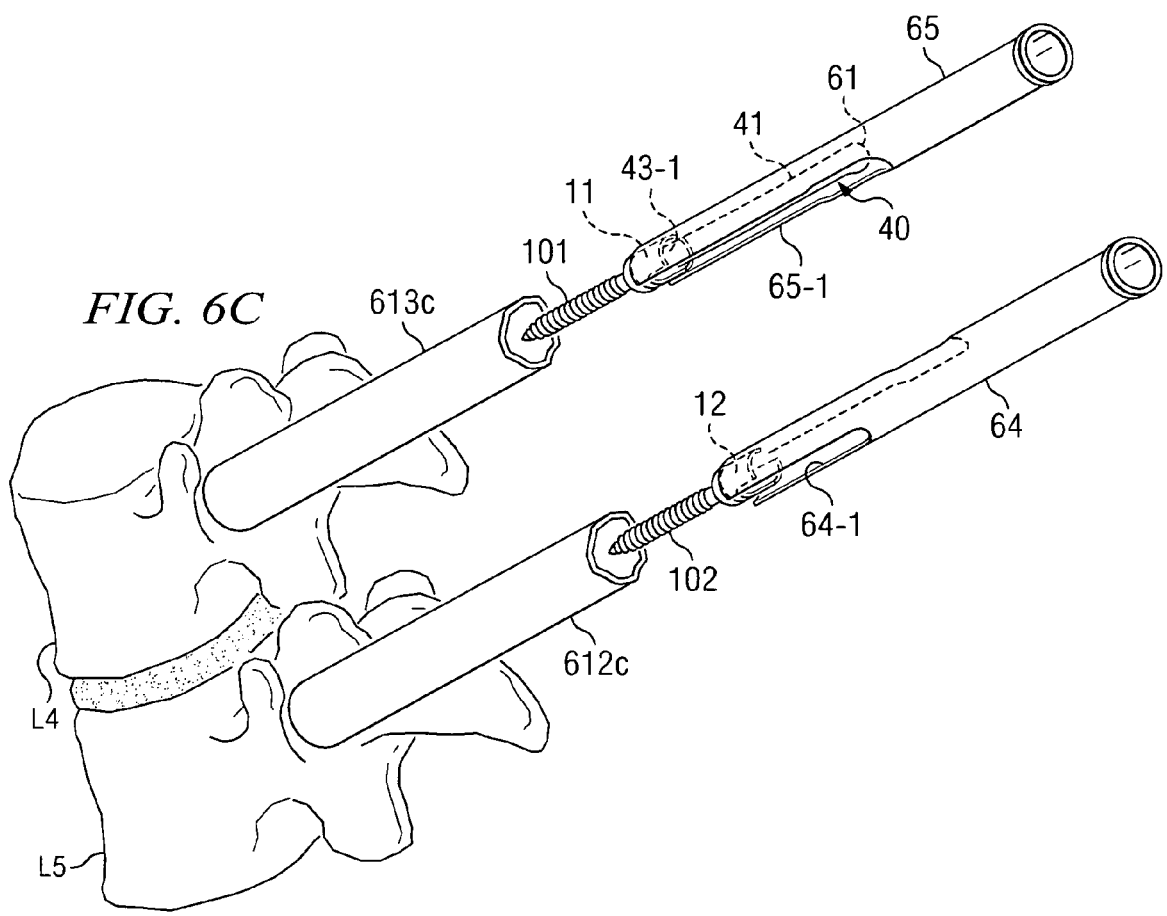

After the hole is tapped and the K wire and the inner dilators, such as dilators 613, 613a, 613b, are removed, the surgeon is ready to introduce the anchor into the vertebrae. As shown in FIG. 6C, prior to inserting the anchor (e.g., pedicle screw), dynamic brace 40 is attached to screw 101 to form a brace-screw assembly. This assembly is then positioned at the distal end of cannula 65 and a screwdriver or wrench is inserted into cannula 65 and attached to proximal end 61 of dynamic brace 40. The entire assembly is then inserted into dilator 613C. The screwdriver engages with proximal end 61 of dynamic brace 40 so as to allow the surgeon to screw pedicle screw 101 into the pre-tapped hole in vertebrae L4. Pressure on the screwdriver forces the screw to be in-line with the dynamic brace, which, in turn, is in-line with the screwdriver. The screwdriver can be removeably attached to end 61 of dynamic brace 40 by engaging, for example, a flat and/or hole in the brace end.

This same procedure would be repeated for each additional level, in this case level L5, except that screw 102 has assembly 12 affixed thereto. Assembly 12 is adapted to receive proximal end 61 of dynamic brace 40 as will be more fully described herein.

For a single level the above procedure is typically performed first on one side of both vertebral levels and then on the other side. When finished, four pedicle screws are inserted, holding two dynamic braces positioned laterally with respect to the center of the spine.

Once both screws are in place in vertebrae L4 and L5, dilators 612C and 613C are removed and, the surgeon slides a blunt dissection tool into the incision and gently parts the muscle bundle below the skin (or cuts a slit in the skin if necessary) between vertebrae. Alternatively, the blunt dissection tool could go down the second cannula and, starting at the bottom of the second cannula work open the muscle bundle between the cannula working upward as far as is necessary. Using this procedure, the muscles (and other tissue), only need be separated to a point where the dynamic brace 40 must pass. Thus, the separation need not go to the skin level. This reduces trauma even further.

Figure 6D:
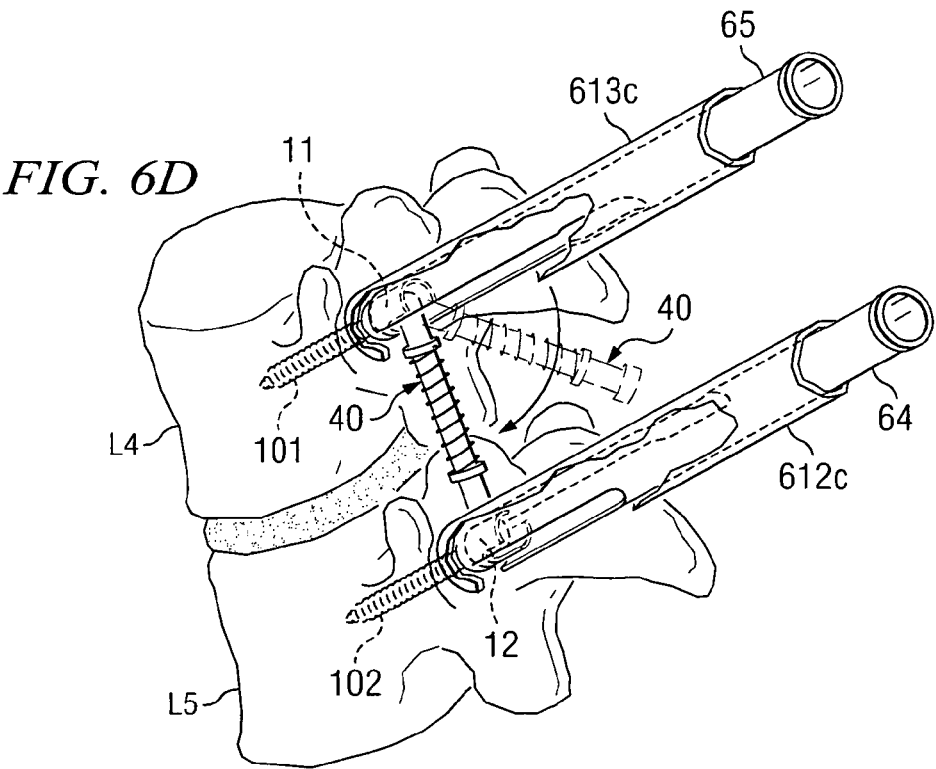

Once an opening in the muscles (or in the skin if desired) has been developed between cannulas 64 and 65, dynamic brace 40 is then positioned, by pivoting, as shown in FIG. 6D, by sliding a tool down cannula 65 to engage proximal end 61 of dynamic brace 40. The tool could have a force fit with end 61 or a handle for controlling removable attachment with dynamic brace 40. Once the tool is mated with end 61 of dynamic brace 40 the surgeon can pull the tool slightly outward to disengage brace end 43-1 from screw 101. Brace end 61 is forced out of cannula 65 (through opening 65-1 thereof) and through the prepared muscle opening and into opening 64-1 of cannula 64. Once within cannula 64, the surgeon, manipulates brace end 61 down cannula 64 and into a mating relationship with screw 102. Once this mating relationship is achieved, the tool is released from brace end 61 and the tool is removed from both cannulas.

The surgeon receives positive feedback (a sensory event), either by feel (for example, a snap action) or by sound (for example, a click), or both when dynamic brace 40 is properly mated with assembly 12. If desired, one or both of assembly 12 or 11 mounted to the respective pedicle screws 102 and 101 can be angularity adjusted to accommodate the patient's body structure. The polyaxial nature of assemblies 102 and 101 with respect to the anchors allows for such adjustments which are necessary for a variety of reasons, one of which is that the angulation between adjacent vertebral pedicles varies.

Figure 6E:
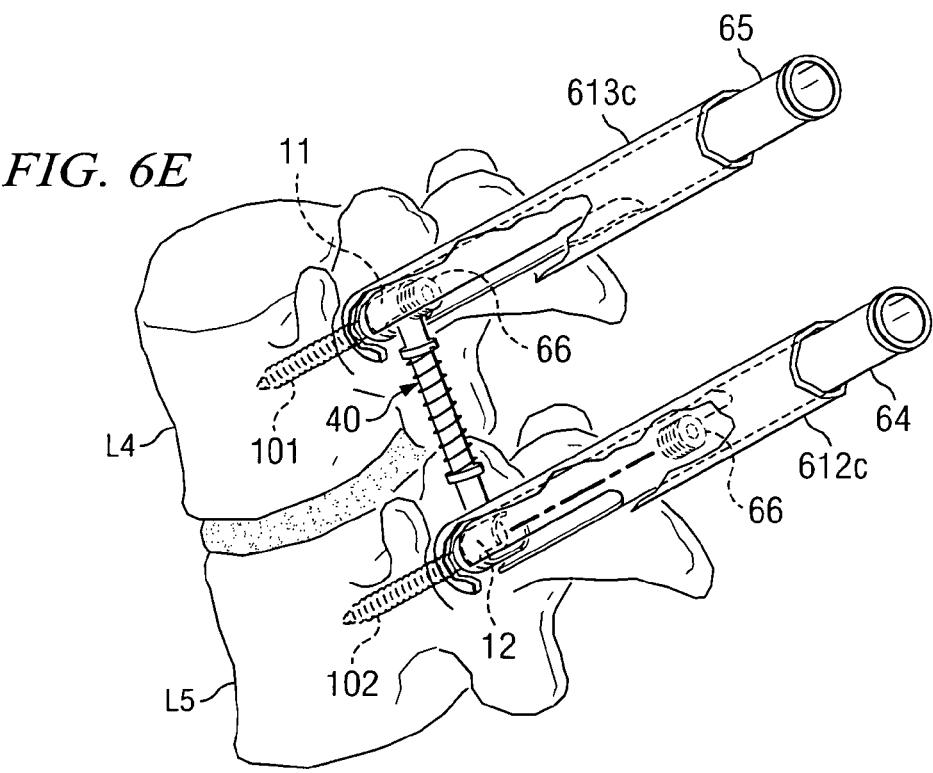

As shown in FIG. 6E, after all angular and lateral adjustments are made, set screws 66, or other locking devices, are introduced down cannulas 64 and 65 to lock each end of dynamic brace 40 to its respective pedicle screw. As discussed above, this establishes the y-axis adjustment of the dynamic brace.

Figure 6F:
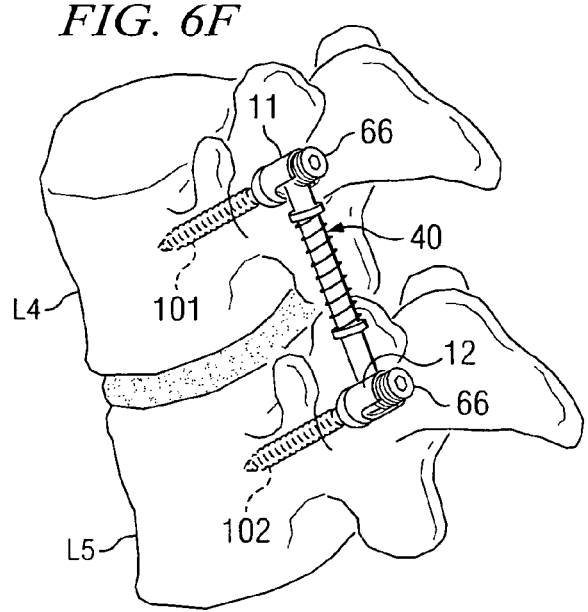

As shown in FIG. 6F, once the proximal end of dynamic brace 40 is snapped in place to screw 102 and set screws 66 are tightened, cannulas 64 and 65 can be removed and the incision closed.

Figure 7:
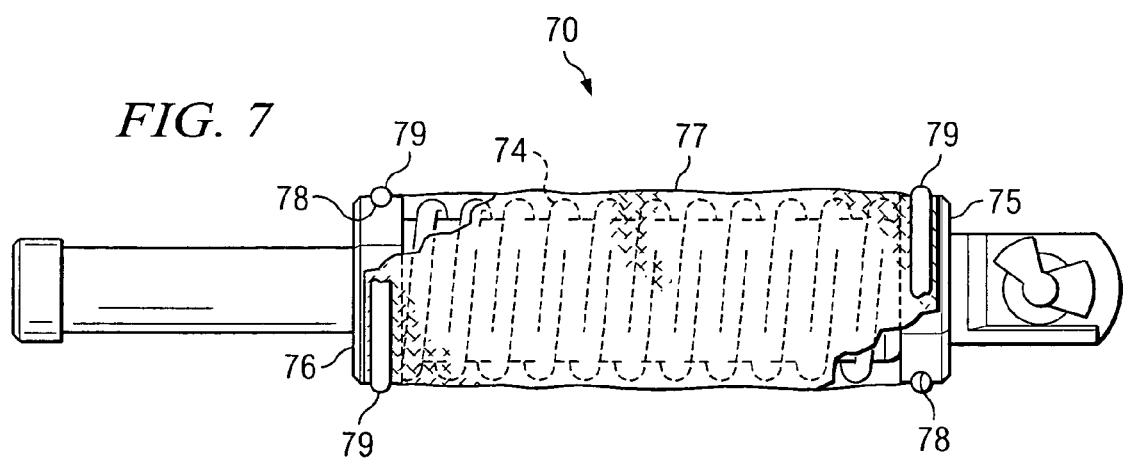
FIG. 7 shows one embodiment of a dynamic stabilization device having a cover thereon.

FIG. 7 shows alternative embodiment 70 of a dynamic stabilization device having cover 77 surrounding spring 74. In this embodiment, the ends of cover 77 are held to stops 75 and 76 by rings 79 fitted into slots 78. The cover is used to protect the device from being interfered with once implanted. Cover (or sleeve) 77 can be constructed from fabric and/or polyester, as examples.

Figure 8A:
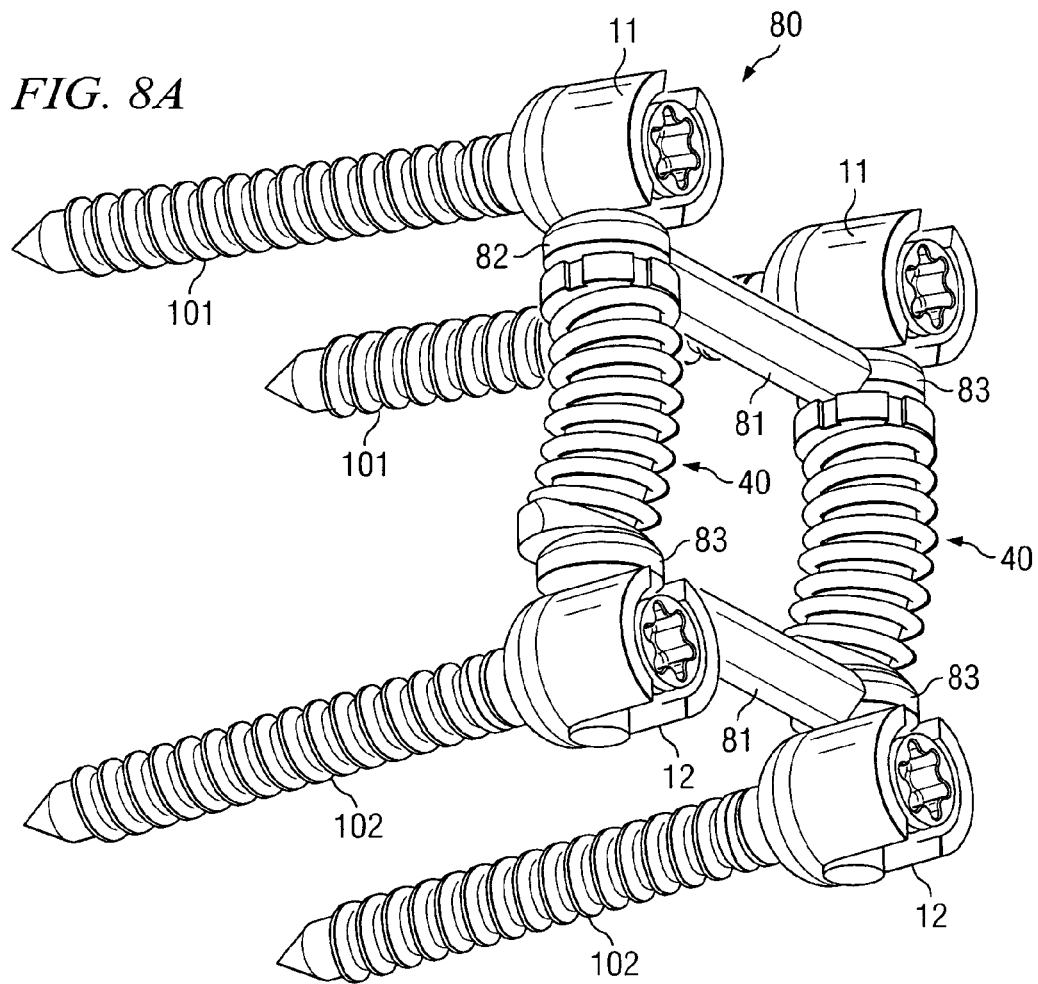
FIGS. 8A and 8B show one embodiment of a cross-connector between a pair of dynamic braces.
Figure 8B:
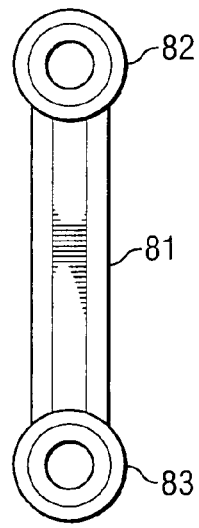

FIG. 8A shows a pair of devices 40 interconnect with one or more cross-connectors 81. The cross-connectors can be fixed or adjustable, and straight or curved as desired, and could be a bar or plate or a tube as shown. The cross-connector acts to combine individual dynamic stability, has devices into a single assembly and will serve to provide a more fluid motion. The cross-connects can be individual, as shown in FIG. 8B with openings to ends 82 and 83 to go around members 41, 42 or device 40 or the entire unit can be constructed as a unit, if desired Note that in any of the embodiments shown, the spring force can be increased to a point where the device effectively becomes static in order to achieve fusion. Also, one or more holes could be positioned through the slide portions such that when a pin is inserted through the holes, the pin effectively prevents the brace from further expansion or contracting. For example, with reference to FIG. 3A, pin 330 could be pushed through holes 331 and 332, in portions 31 and 33. The pin could, for example, have spring loaded balls (or any other mechanism) that serve to prevent the pin from easily pulling out of device 30 once inserted. In addition, the spacing stop 36 could be tightened, either permanently or on a temporary basis, to a point where spring tension effectively places the device in a static condition in order to promote fusion of the treated vertebrae in situations where motion preservation fails to meet surgical end-goals.

Note also that with this device it is possible to take neutral zone displacement readings so as to be able to tension the device properly with respect to a patient. Based on the readings, both the X and Y axis can be adjusted. A dynamic stabilization system should be sensitive to proper placement of the device to restore proper kinematics and full range of motion, and avoid causal deleterious effects of increasing rate of degeneration on adjacent segments. A neutral zone device is a device that can aid in the placement of the dynamic stabilization device by determining the center of rotation in flexion/extension. Once this center of rotation has been determined, the device can be located to best reproduce that center of rotation. The neutral zone device will cycle the spine through a range of motion measuring forces throughout the range of motion. Also, the device can be used after device implantation to confirm proper implant placement.

The curvilinear guides discussed herein reproduce the natural motion of the spine while still. As shown herein, a pair of curvilinear guides (one female and one male) is used to create a curvilinear path of the pedicles which creates, restores and controls the normal center of rotation. Other embodiments that would produce the proper motion could include; for example:

a) a guide bar comprising a pair of pins articulating in a matching pair slots where the slots would diverge to produce a curvilinear motion of a point on the guide bar;
b) a pair of curvilinear plates with attachment means for bone anchors;
c) any type of curvilinear guides made up of male and female shapes following a curvilinear path with a geometric cross section (i.e. dovetail, T-slot, round, square, rectangle, etc. cross section geometry);
d) a four or five bar mechanism that would produce a curvilinear path of the pedicle screw.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method for stabilizing a spine; said method comprising:
   creating two holes, each hole laterally created through adjacent spinal processes;
   positioning a pair of dynamic stabilizers such that one stabilizer is on either side of said spinous process, wherein each of said dynamic stabilizers comprise a first portion and a second portion positioned and configured with respect to said first portion such that the combined longitudinal lengths of the combined first and second portions contract and expand non-linearly along a controlled curvilinear path to maintain a center of rotation;
   inserting a connecting rod through one of said holes such that said connecting rod centers one end of each of said stabilizers with respect to said hole;
   positioning said pair of dynamic stabilizers such that the vertebrae to which they are attached move along a natural arc in flexion and extension upon implantation;
   coupling said connecting rod to one end of each stabilizer so that said stabilizers tightly contact said spinous process on each side thereof;
   repeating said inserting and coupling with respect to the other of said holes; and
   moving a stop on said dynamic stabilizers after said coupling to control in part the distraction force on a spine.

2. The method of claim 1 wherein the moving the stop decreases a tension force on a spring.

3. The method of claim 1 wherein the moving the stop increases a tension force on a spring.

4. The method of claim 1 further comprising aligning the stop with at least one mark on the pair of dynamic stabilizers.

5. The method of claim 1 further comprising taking neutral zone readings to determine proper placement or tensioning of the dynamic stabilizers.

6. The method of claim 5 wherein the taking of neutral zone readings is performed prior to moving the stop.

7. The method of claim 5 wherein the taking of neutral zone readings is performed after moving the stop.

8. The method of claim 1, wherein said first portion of each of said dynamic stabilizers comprises a curvilinear guide slideably mated to said second portion.

9. A method for stabilizing a spine, said method comprising:
   creating two holes, each hole laterally created through adjacent spinal processes;
   positioning a pair of dynamic stabilizers such that one stabilizer is on either side of said spinous process, wherein each of said dynamic stabilizers comprise a first portion and a second portion positioned and configured with respect to said first portion such that the combined longitudinal lengths of the combined first and second portions contract and expand non-linearly along a controlled curvilinear path to maintain a center of rotation;
   inserting a connecting rod through one of said holes such that said connecting rod centers one end of each of said stabilizers with respect to said hole;
   positioning said pair of dynamic stabilizers such that the vertebrae to which they are attached move along a natural arc in flexion and extension upon implantation,
   securing said connecting rod so that said stabilizers tightly contact said spinous process on each side thereof;
   repeating said inserting and securing with respect to the other of said holes; and
moving at least one stop on said dynamic stabilizers to increase in part the distraction force on a spine.

10. The method of claim 9, wherein said first portion of each of said dynamic stabilizers comprises a first portion having a curvilinear guide slideably mated to said second portion.

11. A method for stabilizing a spine, said method comprising:
   creating two holes, each hole laterally created through adjacent spinal processes;
   positioning a pair of dynamic stabilizers such that one stabilizer is on either side of said spinous process, wherein each of said dynamic stabilizers comprise a first portion and a second portion positioned and configured with respect to said first portion such that the combined longitudinal lengths of the combined first and second portions contract and expand non-linearly along a controlled curvilinear path to maintain a center of rotation;

inserting a connecting rod through one of said holes such that said connecting rod centers one end of each of said stabilizers with respect to said hole;

positioning said pair of dynamic stabilizers such that the vertebrae to which they are attached move along a natural arc in flexion and extension upon implantation;

securing said connecting rod so that said stabilizers tightly contact said spinous process on each side thereof;

repeating said inserting and securing with respect to the other of said holes; and adjusting a distraction force of at least one of the dynamic stabilizers to a predetermined value by aligning at least one stop on said dynamic stabilizers with a mark on said dynamic stabilizers.

12. The method of claim 11, wherein said first portion of each of said dynamic stabilizers comprises a first portion having a curvilinear guide slideably mated to said second portion.

* * * * *